United States Patent
Qi et al.

(10) Patent No.: US 11,982,779 B2
(45) Date of Patent: May 14, 2024

(54) METHOD AND APPARATUS FOR GUIDED PAIRING OF MULTI-COINCIDENCES FOR TIME OF FLIGHT POSITRON EMISSION TOMOGRAPHY

(71) Applicant: CANON MEDICAL SYSTEMS CORPORATION, Otawara (JP)

(72) Inventors: Wenyuan Qi, Vernon Hills, IL (US); Yi Qiang, Vernon Hills, IL (US); Peng Peng, Vernon Hills, IL (US); Evren Asma, Vernon Hills, IL (US); Jeffrey Kolthammer, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 433 days.

(21) Appl. No.: 17/230,372

(22) Filed: Apr. 14, 2021

(65) Prior Publication Data
US 2022/0335664 A1    Oct. 20, 2022

(51) Int. Cl.
*G01T 1/29* (2006.01)
*G01T 1/202* (2006.01)

(52) U.S. Cl.
CPC ............ *G01T 1/2907* (2013.01); *G01T 1/202* (2013.01); *G01T 1/2985* (2013.01)

(58) Field of Classification Search
CPC ...... G01T 1/2907; G01T 1/202; G01T 1/2985
See application file for complete search history.

(56) References Cited

U.S. PATENT DOCUMENTS

| | | | |
|---|---|---|---|
| 6,255,655 B1 * | 7/2001 | McCroskey | G01T 1/172 |
| | | | 250/363.04 |
| 2007/0040122 A1 * | 2/2007 | Manjeshwar | G01T 1/2985 |
| | | | 250/363.03 |

(Continued)

FOREIGN PATENT DOCUMENTS

WO    WO 2013/188011 A1    12/2013

OTHER PUBLICATIONS

Extended European Search Report dated Sep. 8, 2022 in European Patent Application No. 22168511.8, 11 pages.

(Continued)

*Primary Examiner* — Hugh Maupin
(74) *Attorney, Agent, or Firm* — Oblon, McClelland, Maier & Neustadt, L.L.P.

(57) ABSTRACT

A guided pairing method includes generating a singles list by detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determining all coincidences possible based on the more than two singles; generating a weight for said each coincidence of the coincidences based on the determined LORs for said each of the two singles of the plurality of singles; and (Continued)

pairing the more than two singles based on the generated weight for said each coincidence of the coincidences.

20 Claims, 12 Drawing Sheets

(56) References Cited

U.S. PATENT DOCUMENTS

| | | |
|---|---|---|
| 2012/0290519 A1* | 11/2012 | Fontaine ............... G01T 1/2985 |
| | | 250/252.1 |
| 2015/0185339 A1 | 7/2015 | Lage et al. |
| 2015/0192685 A1 | 7/2015 | Griesmer et al. |
| 2015/0289825 A1 | 10/2015 | Lage et al. |
| 2016/0131774 A1* | 5/2016 | Lage .................... A61B 6/5217 |
| | | 600/425 |
| 2016/0370474 A1* | 12/2016 | Herraiz ................ A61B 6/4266 |
| 2017/0276809 A1 | 9/2017 | Smith et al. |
| 2018/0114346 A1* | 4/2018 | Sun ....................... G06T 11/005 |

OTHER PUBLICATIONS

Eduardo Lage, et al., "Recovery and nomalization of triple coincidences in PET," Medical Physics, vol. 42, No. 3, XP012195023, Mar. 2015, pp. 1398-1410.

* cited by examiner

METHOD AND APPARATUS FOR GUIDED PAIRING OF MULTI-COINCIDENCES FOR TIME OF FLIGHT POSITRON EMISSION TOMOGRAPHY

FIELD OF THE INVENTION

This disclosure relates to a method and system for guided pairing of multiple coincidences having at least two detected singles in a predetermined detection window.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Positron emission tomography (PET) is a functional imaging modality that is capable of imaging biochemical processes in humans or animals through the use of radioactive tracers. In PET imaging, a tracer agent is introduced into the patient to be imaged via injection, inhalation, or ingestion. After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

During this process, a tracer attached to the agent will emit positrons. When an emitted positron collides with an electron, an annihilation event occurs, wherein the positron and electron are combined. Most of the time, an annihilation event produces two gamma rays (at 511 keV) traveling at substantially 180 degrees apart. The two gamma rays, each known as a single, are detected by detector elements to produce a pair of coincidences. However, measured coincidences include both true coincidences and random coincidences.

In PET scanners, the singles-pairing can be performed with hardware coincidence circuitry, where a multi-photon coincidence event (i.e., more than two singles that are in coincidence) are often rejected and only two-photon coincidence events meeting strict criteria are accepted. With a higher count rate, the multi-photon coincidence event rate will increase significantly, and simply rejecting all the multi-photon coincidence events can lead to massive loss of true coincidence events. Therefore, it is better to retain the multi-photon coincidence events so as to increase the noise equivalent count rate (NECR). While both methods of wholly accepting or rejecting all multi-photon coincidence events yields similar image quality, random events and scatter events are also increased by accepting all multi-photon coincidence events, which leads to collateral degradation of image data. Thus, a method to identify and select the true coincidences from among the set of multi-coincidences is desired.

SUMMARY

The present disclosure relates to a guided pairing method, including generating a singles list by detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determining all coincidences possible based on the more than two singles; generating a weight for said each coincidence of the coincidences based on the determined LORs for said each of the two singles of the plurality of singles; and pairing the more than two singles based on the generated weight for said each coincidence of the coincidences.

The disclosure additionally relates to an imaging apparatus, including generate a singles list by detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determine all coincidences possible based on the more than two singles; generate a weight for said each coincidence of the coincidences based on the determined LORs for said each of the two singles of the plurality of singles; and pair the more than two singles based on the generated weight for said each coincidence of the coincidence.

Note that this summary section does not specify every embodiment and/or incrementally novel aspect of the present disclosure or claimed invention. Instead, this summary only provides a preliminary discussion of different embodiments. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION

Figure 1:
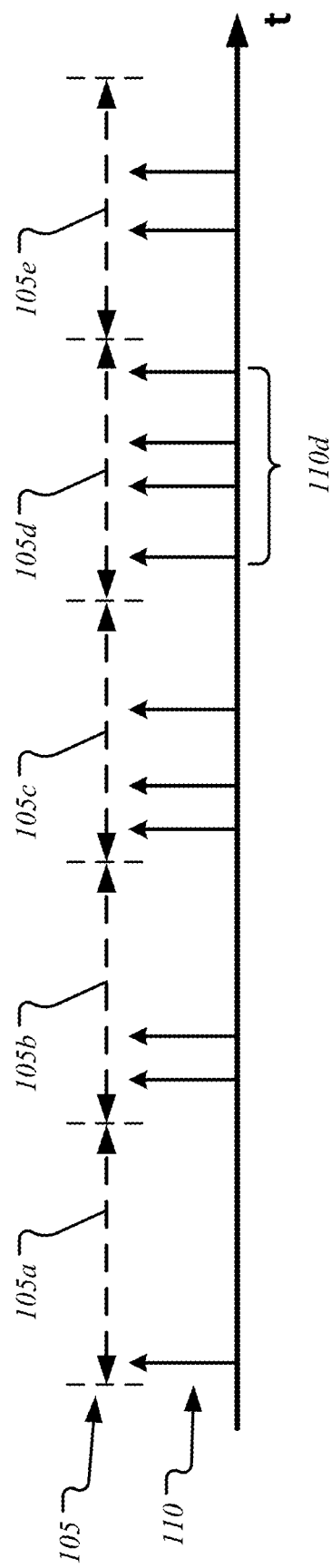
FIG. 1 shows a schematic of an exemplary detected singles list combined for all detector modules over an exemplary time period.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The system may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

According to one embodiment discussed herein, a method for guided pairing of coincidences includes applying weights to all possible coincidences in a multi-photon coincidence event. Notably, the weight applied can be generated based on pairs of 2-photon coincidence events or based on reconstructed images generated from the 2-photon coincidence events.

FIG. 1 shows a schematic of an exemplary detected singles list combined for all detector modules over an exemplary time period. In an embodiment, a single 110 can be detected at a detector module within a predetermined length of time, or a detection window 105. For more than one single 110 detected, a singles list can be compiled showing the detected singles 110 as a function of time. As shown, all of the singles 110 can be separated according to a series of detection windows (generally referred to as 105).

For example, the singles list shown can include a first detection window 105a including one of the singles 110, a second detection window 105b including two of the singles 110, a third detection window 105c including three of the singles 110, a fourth detection window 105d including four of the singles 110, and a fifth detection window 105e including two of the singles 110. It may be appreciated that the predetermined length of time of the individual detection windows 105a-105e can vary and be set according to the imaging system used or based on an operator need/desire. In general, the length of time of the individual detection windows 105a-105e will be equal to one another and can be, for example, 12 ns each. Furthermore, it may be appreciated that the predetermined length of time of the individual detection windows 105a-105e generally result in a majority of the detection windows 105a-105e including two of the singles 110, while a minority include one or more than two of the singles 110. However, as previously described, increasing the count rate can cause there to be an increase in the number of the detection windows 105a-105e including more than two of the singles 110 and thereby increasing the rejection rate of some methods attempting to pair the singles. The method described herein attempts to reduce this rejection rate.

Figure 2A:
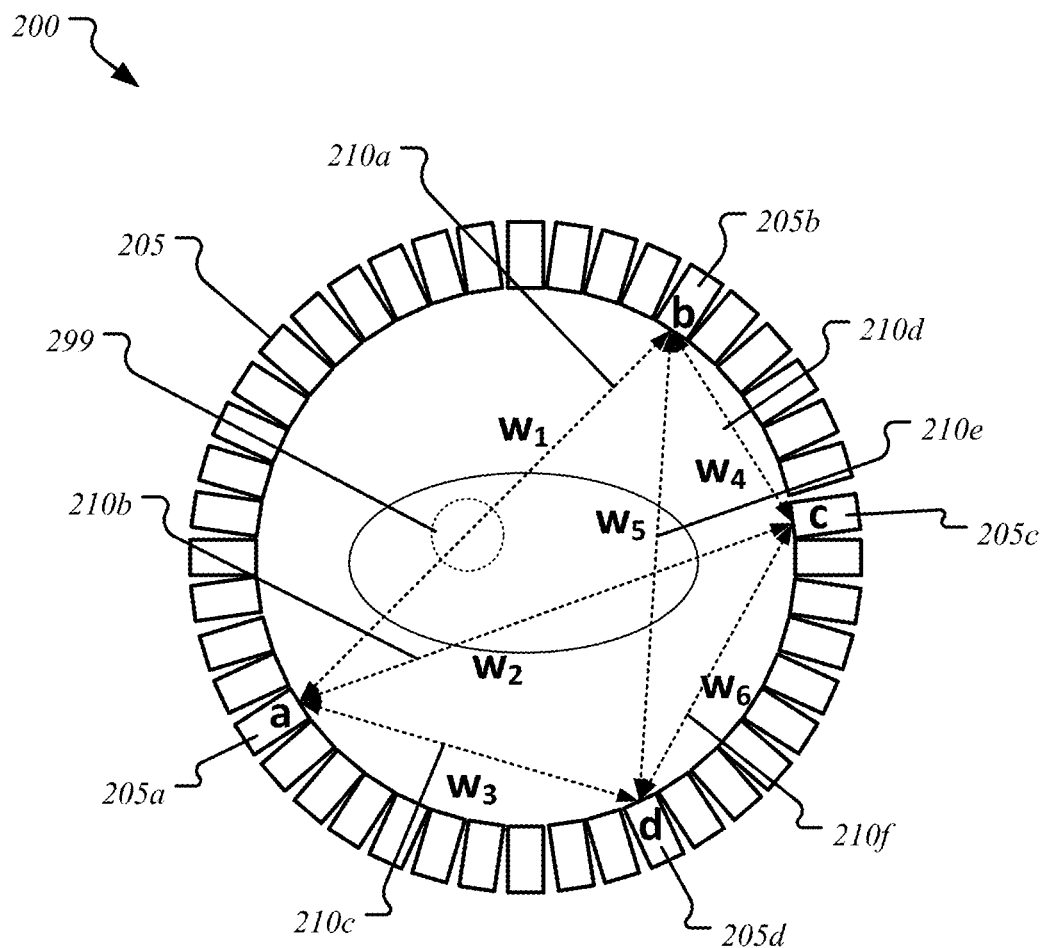
FIG. 2A shows a transaxial cross-sectional schematic of an exemplary positron emission tomography (PET) scanner.
Figure 7A:
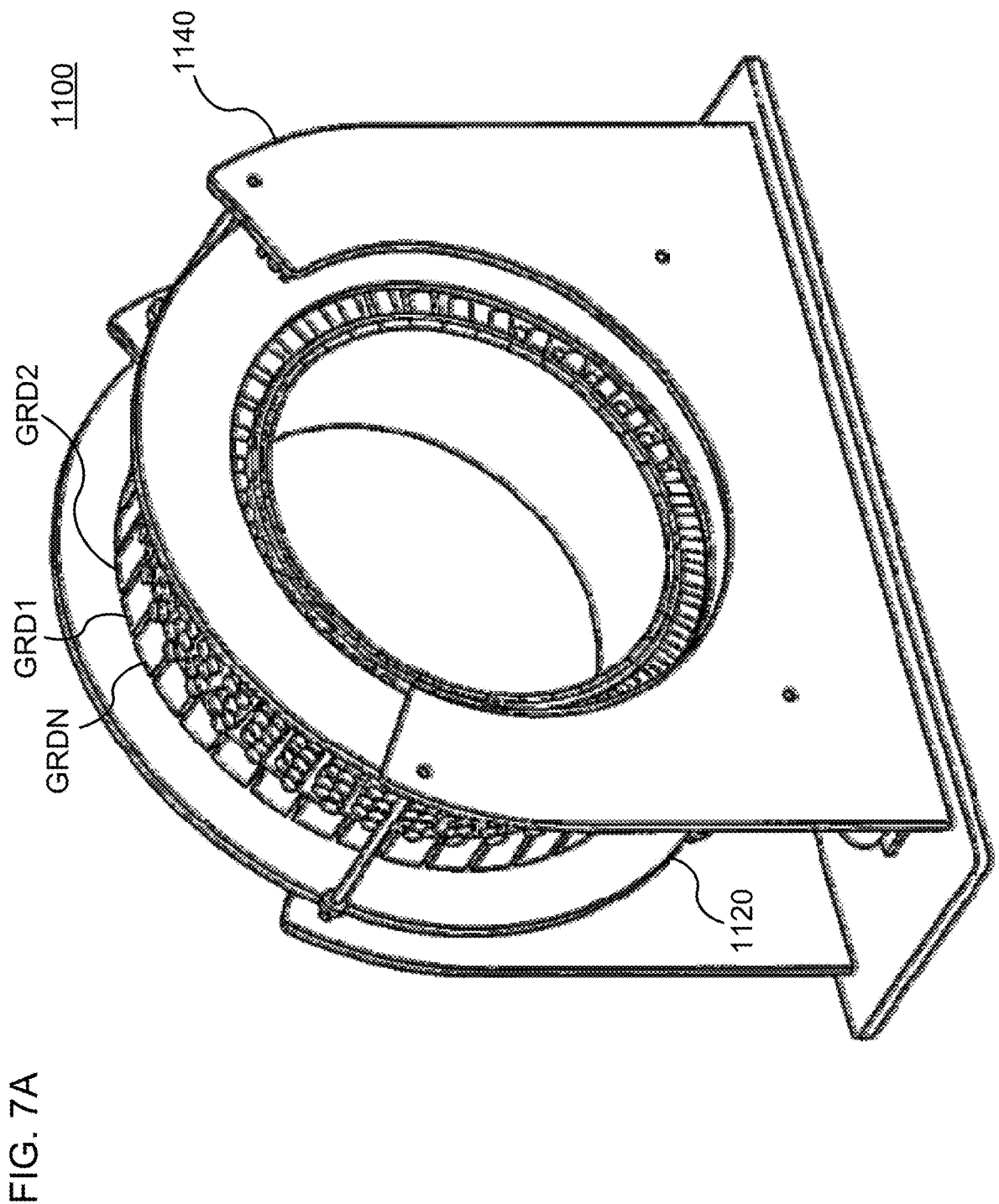
FIG. 7A shows a perspective view of an PET scanner that can be used with the techniques described herein.
Figure 7B:
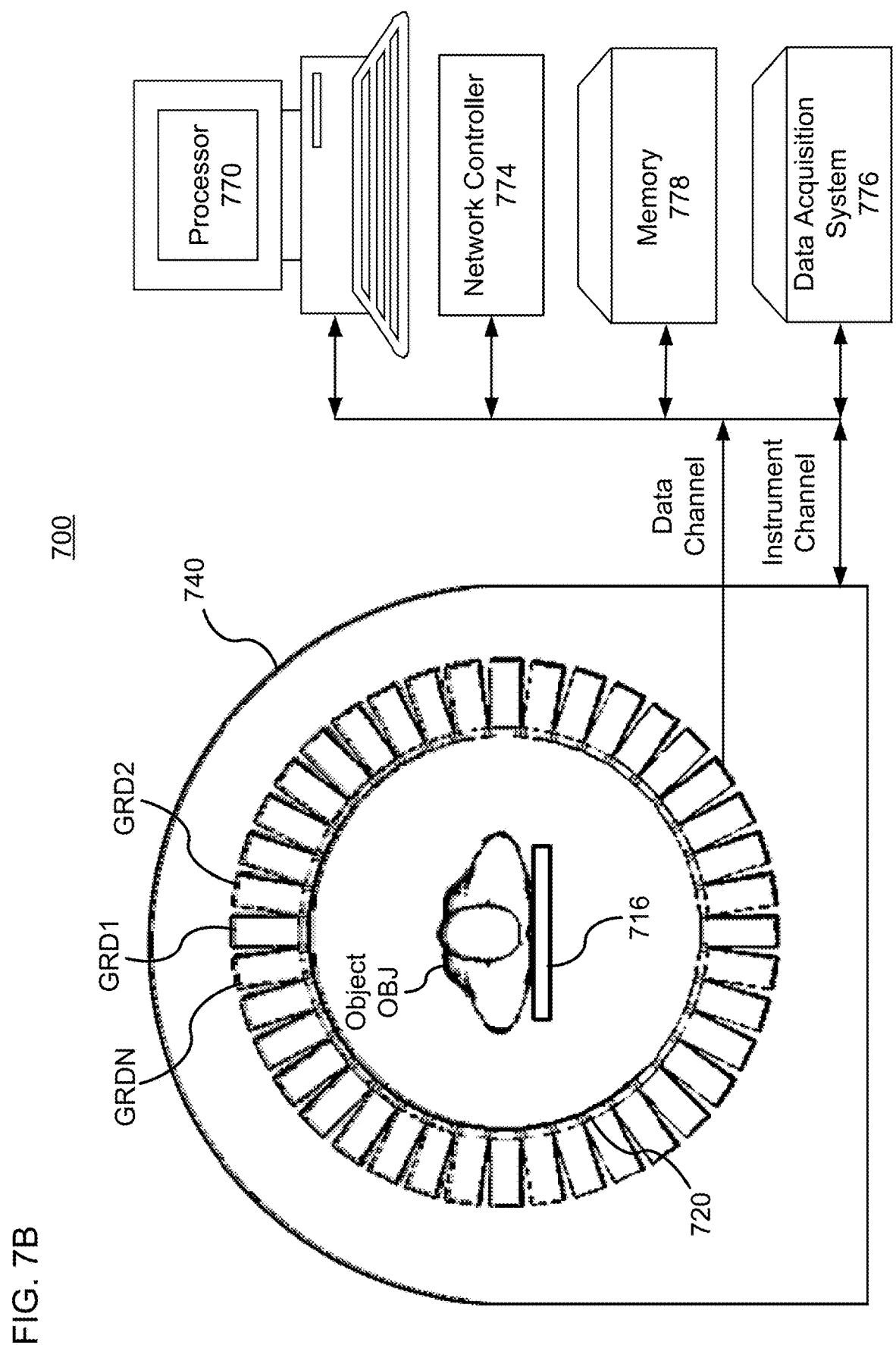
FIG. 7B shows a schematic view of a PET scanner that can be used with the techniques described herein.

FIG. 2A shows an exemplary transaxial cross-sectional schematic of a positron emission tomography (PET) scanner 200. In the exemplary embodiment, the PET scanner 200 includes detector elements 205 arranged in a ring around a central axis that are configured to detect electromagnetic radiation, such as gamma rays. The PET scanner 200 can include additional rings of detector elements 205 disposed along the axis of the rings. Additional PET scanner 100 features are shown in FIGS. 7A and 7B and described in the accompanying description below. An object to be scanned can be arranged in the center of the detector elements 205, such as a phantom or a human. The object can include a high count-emitting region 299, such as a human heart or lung deemed of high importance during imaging.

When an emitted positron from the phantom or human collides with an electron, an annihilation event occurs, wherein the positron and electron are combined. Most of the time, the annihilation event produces two gamma rays (at 511 keV) traveling at substantially 180 degrees apart. One of these gamma rays can be referred to as the single 110. To reconstruct the spatio-temporal distribution of tracers via tomographic reconstruction principles, each detected event is characterized for its energy (i.e., amount of light generated), its location, and its timing. By detecting the two gamma rays (i.e. two of the singles 110), and drawing a line between their locations (i.e., by calculating a line-of-response (LOR)), one can determine the likely location of the original disintegration.

In one example shown in FIG. 1, during a fourth detection window 105d, four of the singles 110 are detected. That subset will be referred to herein as "the singles subset" 110d. An exemplary corresponding process of spatially detecting the singles subset is shown in FIG. 2A. All possible combinations of pairing the singles subset 110d are shown wherein pairs of two of the singles subset 110d traveling at substantially 180 degrees apart from an annihilation event are grouped. Grouped pairs of singles can be referred to as a 2-photon coincidence 210 or simply as a "coincidence 210". For example, a first detector element 205a can detect a first one of the singles subset 110d (labeled "a"), a second detector element 205b can detect a second one of the singles subset 110d (labeled "b"), a third detector element 205c can detect a third one of the singles subset 110d (labeled "c"), and a fourth detector element 205d can detect a fourth one of the singles subset 110d (labeled "d"). Thus, for pairing the singles subset 110d, a combinatorics formula of "N Choose 2" or $NC_2$ can be used to determine the maximum possible number of the 2-photon coincidences 210. Concomitantly, for all four of the singles subset 110d, a maximum possible number of the coincidences 210 is six. In the same example as shown, the six possible coincidences 210 are labeled such that: a first coincidence 210a is the coincidence between detector elements "a" and "b", a second coincidence 210b is the coincidence between detector elements "a" and "c", a third coincidence 210c is the coincidence between detector elements "a" and "d", a fourth coincidence 210d is the coincidence between detector elements "b" and "c", a fifth coincidence 210e is the coincidence between detector elements "b" and "d", and a sixth coincidence 210f is the coincidence between detector elements "c" and "d".

In most PET scanners, more than two detected singles 110 in the same detection window, such as the fourth detection window 105d, would lead to rejection of the data since a true coincidence (i.e. the coincidence 210 having the true origin of the annihilation along the LOR) cannot be determined. In others, all of the more than two detected singles 110 can be accepted.

To keep all of the singles 110 in an event having detected more than two singles 110, a first detected single is paired with all possible subsequent detected singles that fall within the detection window 105. Then the same pairing process is iterated for the next detected single within the detection window 105 until all detected singles in the detection window 105 are exhausted. This process is iterated for all the remaining detected singles until all detected singles in the detected singles list are exhausted.

To reject all of the singles 110 in the event having detected more than two singles 110, the first detected single is counted along with all subsequent singles falling within the same detection window 105. Upon determining only one other of the single 110 exists in the detection window 105, the two singles 110 are paired and determined to be the one possible coincidence. Upon determining more than one other of the single 110 exists in the detection window 105, all of the singles 110 are skipped without any pairing. The process is then moved to start at the first detected single in a subsequent, new detection window 105. This process is iterated until all detected singles in the detected singles list are exhausted.

However, wholly accepting or rejecting all of the singles 110 without attempting to determine the true coincidences can lead to degradation of image quality and data. Therefore, described herein is a method for determining the true coincidences from a detection event for multiple of the singles 110 while rejecting random coincidences to improve the quality of reconstructed images. While previous methods of accepting and rejecting may be based solely on timing information of the single 110, the method described herein uses guided pairing processes based on applied weights. The weight can be based on the probability of the coincidence in question being the true coincidence. All of the coincidences can be assigned a weight and considered before determining to accept or reject said coincidence in question, which can then be used for final image reconstruction.

Referring again to FIG. 2A, the singles subset 110d are detected by the four detector elements 205 to generate the six coincidences 210a-210f. In general, there can be N detected singles, leading to N Choose 2 ($NC_2$) possible coincidences. In an embodiment, a weight, w, can be assigned to each of the six coincidences 210a-210f. As shown, $w_1$ is assigned to the first coincidence 210a, $w_2$ is assigned to the second coincidence 210b, and so on. To obtain the weights $w_1$ to $w_6$ for the six example coincidences 210a-210f, a number of counts $p_i$ detected along each of the six coincidences 210a-210f can be determined. That is to say, the number of counts detected can be represented by the number of the detection windows 105 including exactly two of the singles 110 detected, wherein said two of the singles 110 detected were detected at said two of the four detector elements 205.

Then, the weights can be determined by:

$$w_i = \frac{1}{T} p_i,$$

where T is a normalization factor to make: $\Sigma_0^N w_i = 1$. Notably, as the first coincidence 210a passes through the high count-emitting region 299, the value of $p_1$ will be higher and therefore the weight $w_1$ of the first coincidence 210a will be concomitantly higher. For example, there can be one hundred of the detection windows 105 including exactly two of the singles 110 detected, wherein ninety of the one hundred cases include the two singles 110 being detected at the first detector element 205a and the second detector element 205b to form ninety counts of the first coincidence 210a. Thus, there is a majority of counts detected forming the first coincidence 210a and therefore the first coincidence 210a can have a higher weight. It may be appreciated that empirically, the first coincidence 210a passes through the object closer to the center and high-value regions (such as lungs, the heart, etc.), the second coincidence passes through the object farther from the center but potentially through high-value regions (such as the lungs), the fifth coincidence 210e passes through the object closer to a periphery and lower-value regions (such as the shoulders), and the third coincidence 210c, fourth coincidence 210d, and sixth coincidence 210f do not pass through the object at all. Thus, empirically, the value of the weights can also be deduced to be: $w_1 > w_2 > w_5 > w_3 > w_4 > w_6$.

Figure 2B:
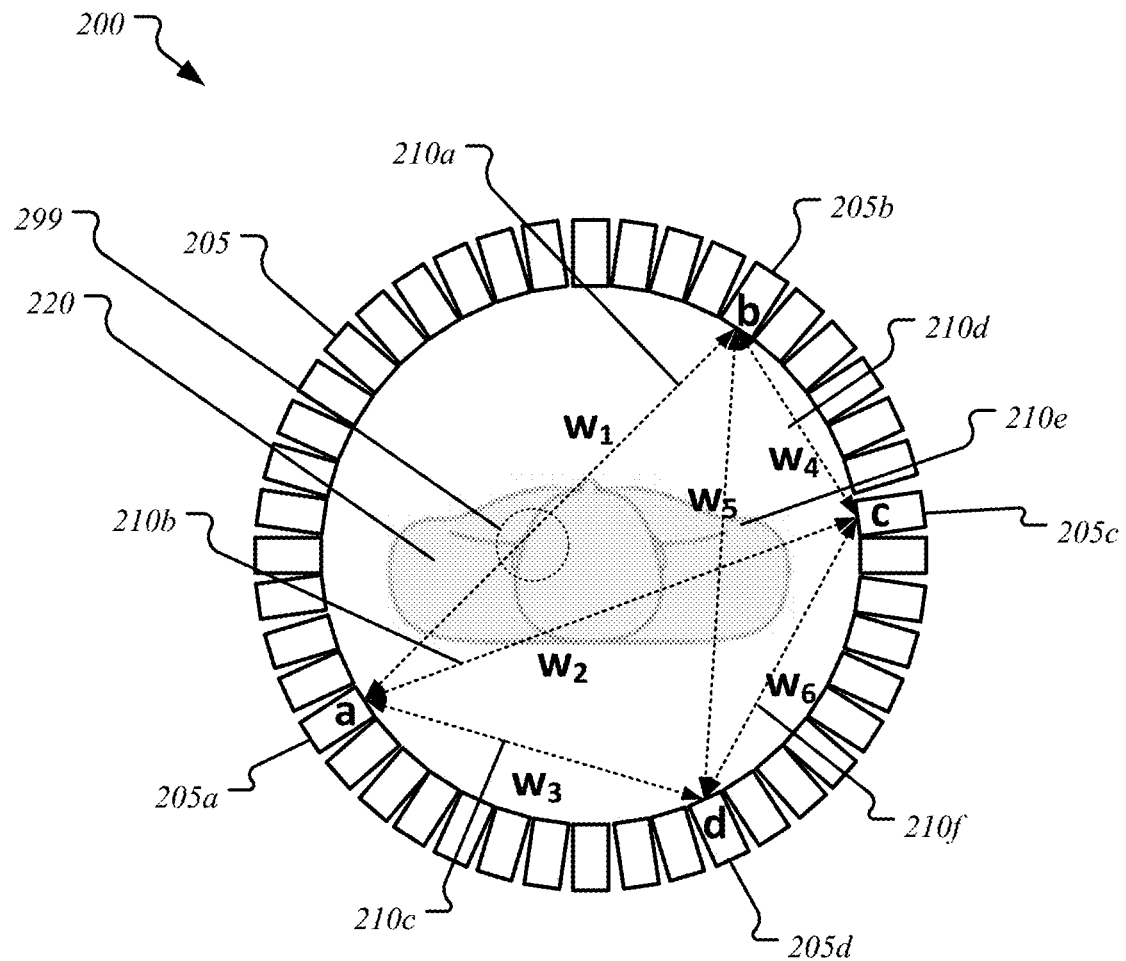
FIG. 2B shows a transaxial cross-sectional schematic of the exemplary PET scanner including a reconstructed image.

FIG. 2B shows a transaxial cross-sectional schematic of the exemplary PET scanner 200 including a reconstructed image 220. In an embodiment, the weights $w_1$ to $w_6$ can be determined by performing a PET reconstruction based on the detection windows 105 including only said two of the singles 110. A random and scatter correction can be applied. However, the reconstructed image 220 can exclude an attenuation correction. Subsequently, the weights can be determined by:

$$w_i = \frac{1}{T}(HX)_j,$$

where H is the system matrix, X is the reconstructed image 220, j is the index of the corresponding coincidence 210 of the whole system, and T is the normalization factor. That is, the weight of the possible coincidence 210 can be based on the forward projection of the reconstructed image 220 to the LOR of the possible coincidence 210. Notably, the high count-emitting region 299 can be confirmed to be a region of high importance for imaging (e.g., a patient's heart), thus further confirming the value of weights to be: $w_1 > w_2 > w_5 > w_3 > w_4 > w_6$.

Figure 2C:
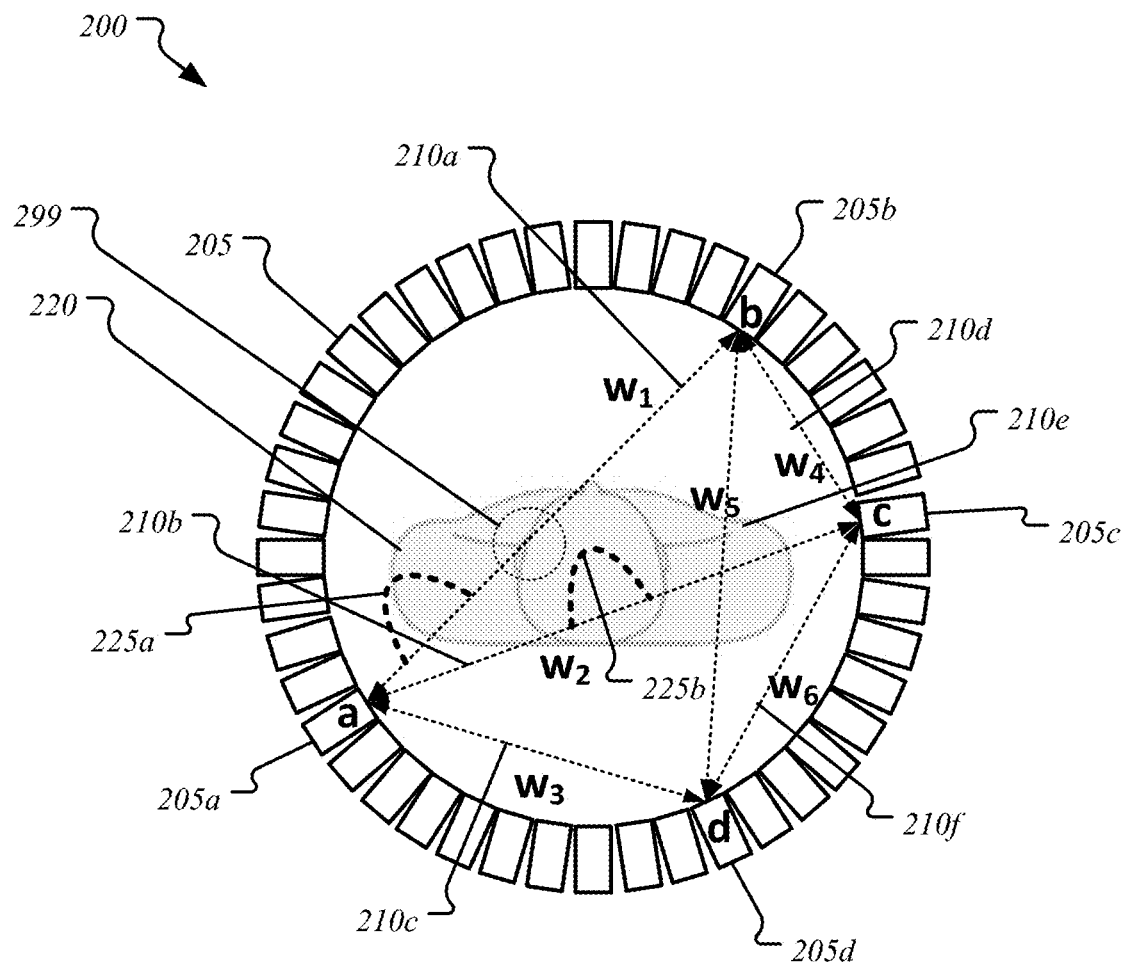
FIG. 2C shows a transaxial cross-sectional schematic of the exemplary PET scanner including the reconstructed image and a time-of-flight (TOF) kernel.

FIG. 2C shows a transaxial cross-sectional schematic of the exemplary PET scanner 200 including the reconstructed image 220 and a first time-of-flight (TOF) kernel 225a and a second TOF kernel 225b. In an embodiment, a PET reconstruction based on the six coincidences 210a-210f is performed to generate the reconstructed image 220. A random and scatter correction can be applied. However, the reconstructed image 220 can exclude an attenuation correction. The weights $w_1$ to $w_6$ can be determined by the forward projection of the reconstructed image 220 within a range of the TOF kernels 225a-225b of the coincidence 210 in question. For each possible pair in FIG. 2C, there is a timing difference between the two events (the singles 110 at the two detectors "a" and "b"). When the weight $w_1$ for the first coincidence 210a is determined, only the image convoluted within the TOF kernel range will be used for the calculation. That is, the weights can be determined by:

$$w_i = \frac{1}{T}(HX^{TOF})_j,$$

where H is the system matrix, $X^{TOF}$ is the reconstructed image 220 convolved with the TOF kernels 225a-225b, j is the index of the corresponding coincidence 210 of the whole system, and T is the normalization factor. Notably, the TOF kernels 225a-225b can further identify the potential origination location of the annihilation event of the coincidence 210. This leads to a significant increase in accuracy as explained as follows.

In an example, the value of weight $w_1$ is greater than $w_2$ for FIG. 2B since the first coincidence 210a appears to pass through the high count-emitting region 299. The same appears to be true for FIG. 2C, however, the first TOF kernel 225a depicted in FIG. 2C provides further clarifying information that the potential origin of the annihilation event of the first coincidence 210a is actually located outside the high count-emitting region 299. Furthermore, the first TOF kernel 225a is actually located only partially within the human's body in the reconstructed image 220 and even partially outside the body altogether. In contrast, the second TOF kernel 225b can be located within the human's body and nearly passing through the center of mass. Without the TOF information, the relative weights would be $w_1 > w_2 > w_5$, and there are more detected counts along the first coincidence 210a as compared to the second coincidence 210b. That is, in the non-TOF scenario, a sum of the image voxel intensities can be calculated which pass through each of the coincidences (210a, 210b, 210e). Then from this image, it can be determined that the sum of the voxel intensities for the first coincidence 210a is larger than sum of the second coincidence 210b and the sum of the fifth coincidence 210e since the first coincidence 210a has a very high count activity from the high count-emitting region 299 (e.g., the heart). Instead, upon introduction of the first TOF kernel 225a and the second TOF kernel 225b (and any other necessary TOF kernels 225 for any other of the coincidences 210), the timing difference elucidates that the location of the origin of the first coincidence 210a would have been mostly outside the body. Furthermore, the sum of the voxel intensities only within the first TOF kernel 225a or the second TOF kernel 225b can be summed. Thus, if the voxel intensities within the second TOF kernel 225b are larger than those of the first TOF kernel 225a, then the weight will be larger, and it can be determined that the opposite is true—that the weight of $w_1 < w_5 < w_2$.

Once all weights have been assigned to each of the coincidences 210, the weights can be used for guided pairing or reconstructions.

In an embodiment, only one coincidence 210 paired for each of the detection windows 105 can be accepted, wherein the coincidence 210 with the highest weight is paired, and all others are rejected. For example, in FIG. 2A, $w_1 > w_2 > w_5 > w_3 > w_4 > w_6$. Thus, only the first coincidence 210a having weight $w_1$ is kept and the other coincidences (210b-210f) are rejected.

In an embodiment, each coincidence 210 is saved by a possibility of $w_i$ or rejected by a possibility of $1-w_i$, wherein $0 < w < 1$. For example, the first coincidence 210a can have a weight $w_1$ of 0.75. To determine whether to accept or reject the first coincidence 210a, a number can be generated having a uniform distribution between 0 and 1. If the generated number is less than or equal to 0.75, the event for the first coincidence 210a is accepted, otherwise the event is rejected.

In an embodiment, all of the possible coincidences 210 can be saved along with their corresponding weights. During sinogram reconstruction, all of the possible coincidences 210 can be multiplied by the corresponding weights to the sinogram. During list-mode reconstruction, the weight for each of the coincidences 210 can be retained and used as a correction factor during iterative reconstruction.

Figure 3:
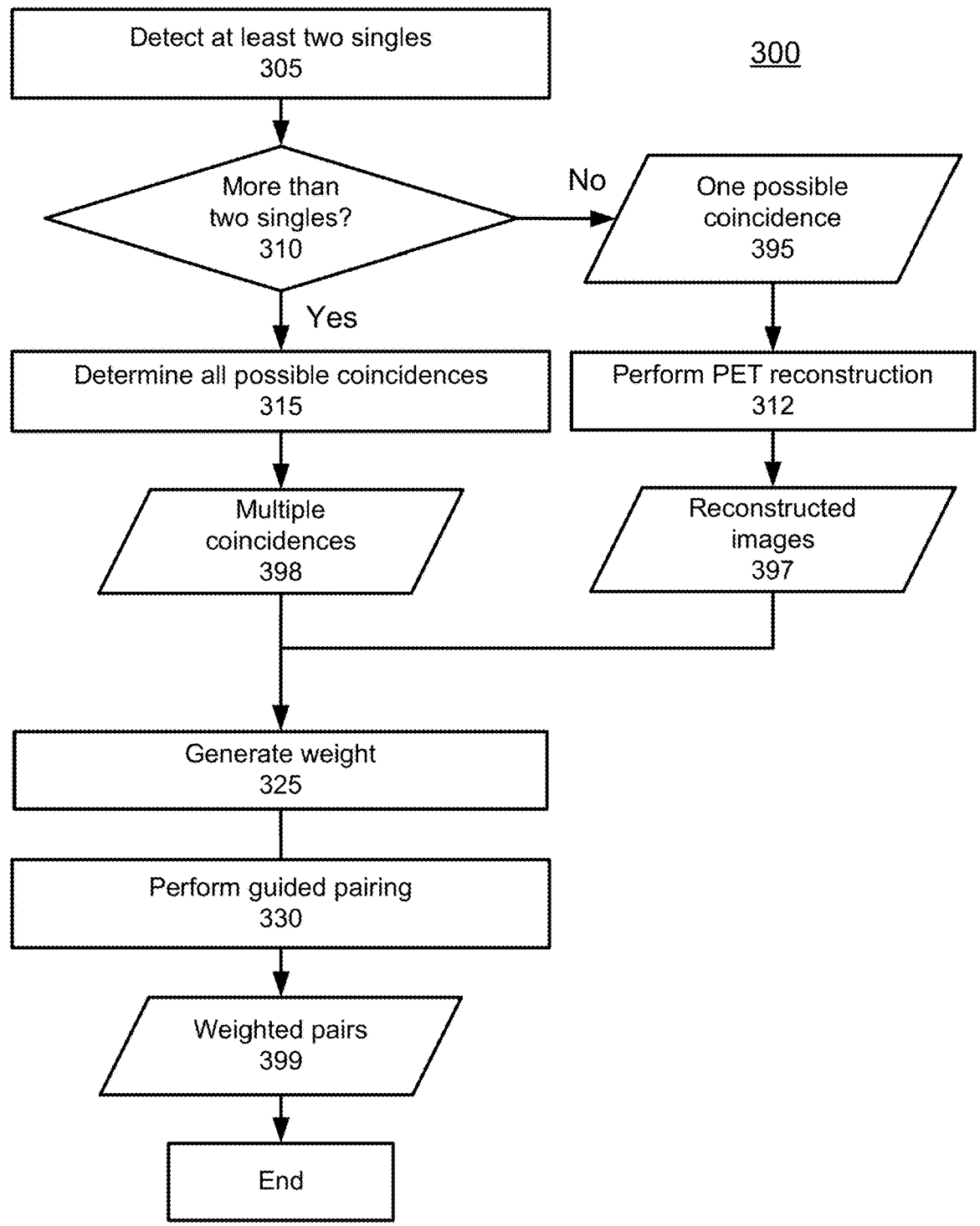
FIG. 3 shows a non-limiting example of a flow chart for a guided pairing method 300 of determining the weighted pairs from among a given set of singles.

FIG. 3 shows a non-limiting example of a flow chart for a guided pairing method 300 of determining the weighted pairs in a detection window from among a given set of singles in that detection window, according to one exemplary embodiment.

In step 305, at least two of the singles 110 are detected in the detection window 105. In an embodiment, when one single 110 is detected within the detection window 105, there is no other single 110 with which to pair the detected single 110, and thus the data is not accepted. When at least two singles 110 are detected, the at least two singles 110 can be paired.

In step 310, upon determining the PET system 100 detected at least two of the singles 110, but not more than two (i.e. exactly two of the singles 110), the two singles 110 can be paired and this yields one possible coincidence 395 since there are no other possible pairings available. In step 312, a PET image reconstruction can be performed based on the one possible coincidence 395.

In step 315, upon determining the PET system 100 detected more than two of the singles 110 in the given detection window 105, all possible pairings of the singles can be performed to determine all possible coincidences 210 from the set of the singles 110 for the given detection window 105 to yield all possible multiple coincidences 398. The maximum number of possible coincidences 210 can be determined via N Choose 2, wherein N is the number of the detected singles 110 in the given detection window. For example, as seen in FIGS. 2A-2C, 4 Choose 2 yields six possible coincidences 210 of the four detected singles 110 at detector elements 205a-205d.

In step 325, a weight for each of the coincidences 210 can be generated. For example, the weight can be based on detected counts or the sum of the voxel intensities along the coincidence 210. Additionally, the weight can be based on the forward projection of the PET image reconstruction of the coincidence 210. For example, the weight can be based on the forward projection of the reconstructed image within the TOF kernel 225 of the coincidence 210.

In step 330, guided pairing of the singles can be performed based on the weighted coincidences 210 to yield weighted pairs 399. The weighted pairs 399 can then be used in generating an updated reconstructed image. In an embodiment, all of the possible coincidences 210 can be saved along with their corresponding weights. During sinogram reconstruction, all of the possible coincidences 210 can be multiplied by the corresponding weights to the sinogram. During list-mode reconstruction, the weight for each of the coincidences 210 can be retained and used as a correction factor during iterative reconstruction.

EXAMPLES

Example 1

To obtain quantitative data in PET, the sum of the true and scattered coincidences can be determined by estimating and subtracting the random coincidences from the measured data in each LOR. The number of random coincidences detected as delayed coincidences will equal, on average, the number of random coincidences in the prompt coincidence sinogram. With a correction for random coincidences, the delayed coincidences are subtracted from the prompt coincidences sinogram as they occur. More precisely, using mean values, P=T+S+R and D=R, so the correction for random coincidences is T+S=P−D, where P, T, S, R, and D are the numbers (or rates) of prompt, true, scattered, random, and delayed coincidences. This provides an accurate correction for random coincidences but also increases statistical noise in the net (prompt)−(delay) coincidence sinogram.

Figure 4A:
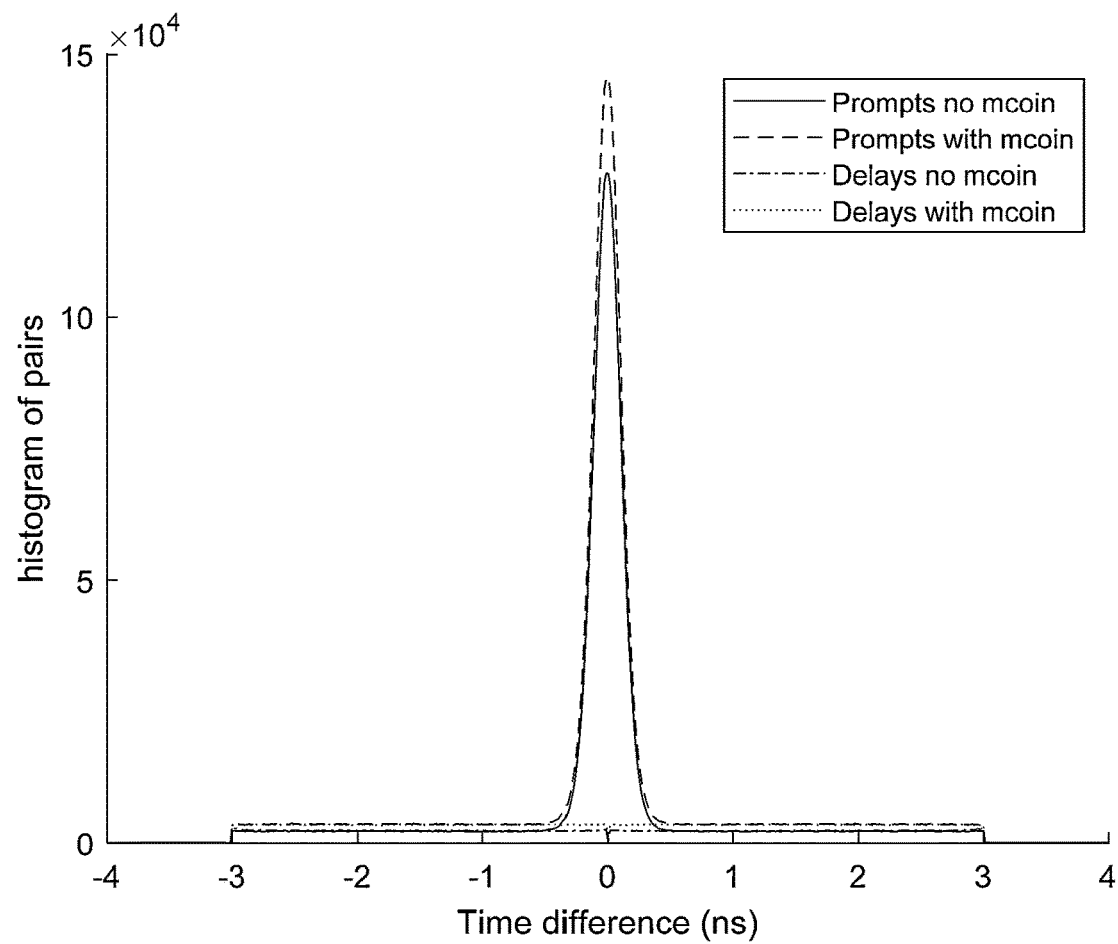
FIG. 4A shows an exemplary graph of the time difference distribution for a real line source.
Figure 4B:
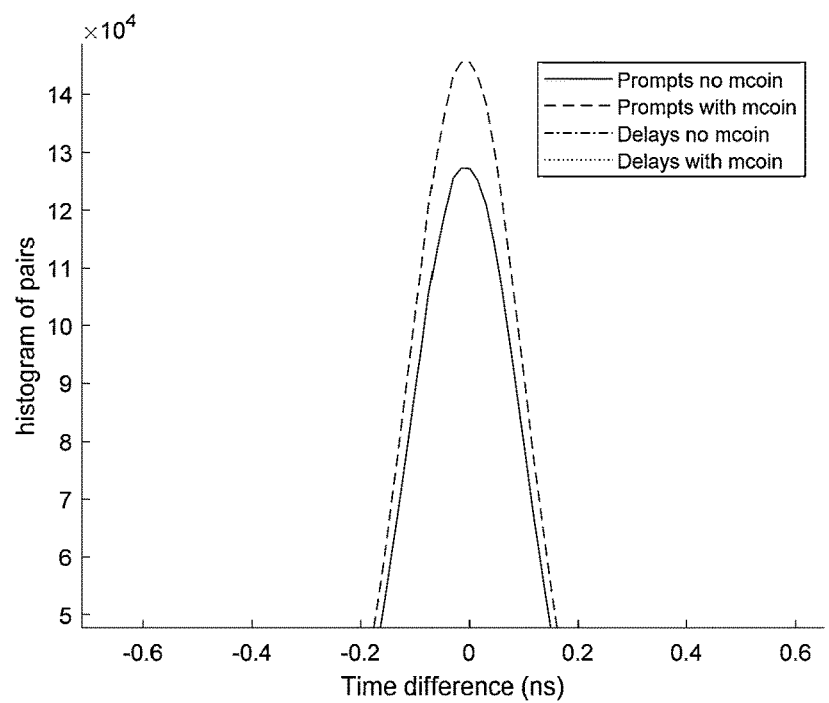
FIG. 4B shows a zoom of the peak for the graph of the time difference distribution shown in FIG. 4A.
Figure 4C:
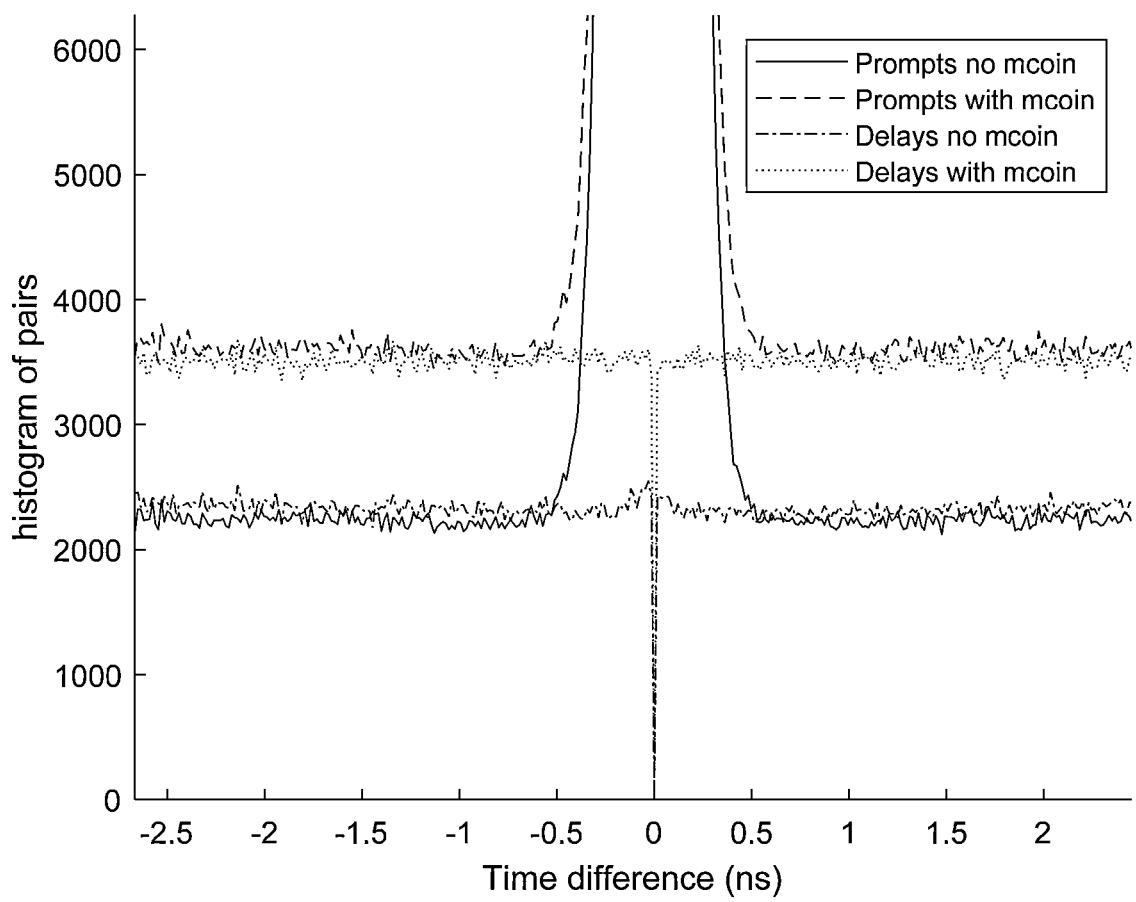
FIG. 4C shows a zoom of the baseline for the graph of the time difference distribution shown in FIG. 4A.

In order to test the effectiveness of the methods described, and validate that prompts and delays have the same distributions for random events (also referred to as "randoms"), a real centered line source was used to test the time difference distribution. Prompts can be understood to mean prompt coincidence events, or those detected within the detection window 105. Delays can be understood to mean delayed coincidence events, wherein the detection window 105 is lengthened greatly compared to the detection window 105 of the detected prompt coincidence events. Notably, the possibility rate of a random event being detected within the detection window (|t1−t2|<tc, t1 and t1 are the times for the two singles, and tc is the detection window size) is the same as for the random event within a delayed detection window (|t1−(t2+td)|<tc, wherein td is a user defined parameter that describes a fixed time difference between two singles. For a real centered line source, a graph of the time difference distribution is shown in FIG. 4A, according to one exemplary embodiment. FIG. 4B shows a zoom of the peak for the graph of the time difference distribution shown in FIG. 4A, according to one exemplary embodiment. FIG. 4C shows a zoom of the baseline for the graph of the time difference distribution shown in FIG. 4A, according to one exemplary embodiment. Note that FIG. 4A does not include guided pairing results and is presented to demonstrate baseline data for accepting all the coincidences (see "with mcoin") or rejecting all the coincidences (see "no mcoin").

By using the disclosed guided pairing method, more true events are generated and randoms are reduced. Data demonstrating the effectiveness of the disclosed method is shown in FIG. 5A-5C, including the baseline data of FIGS. 4A-4C.

Figure 5A:
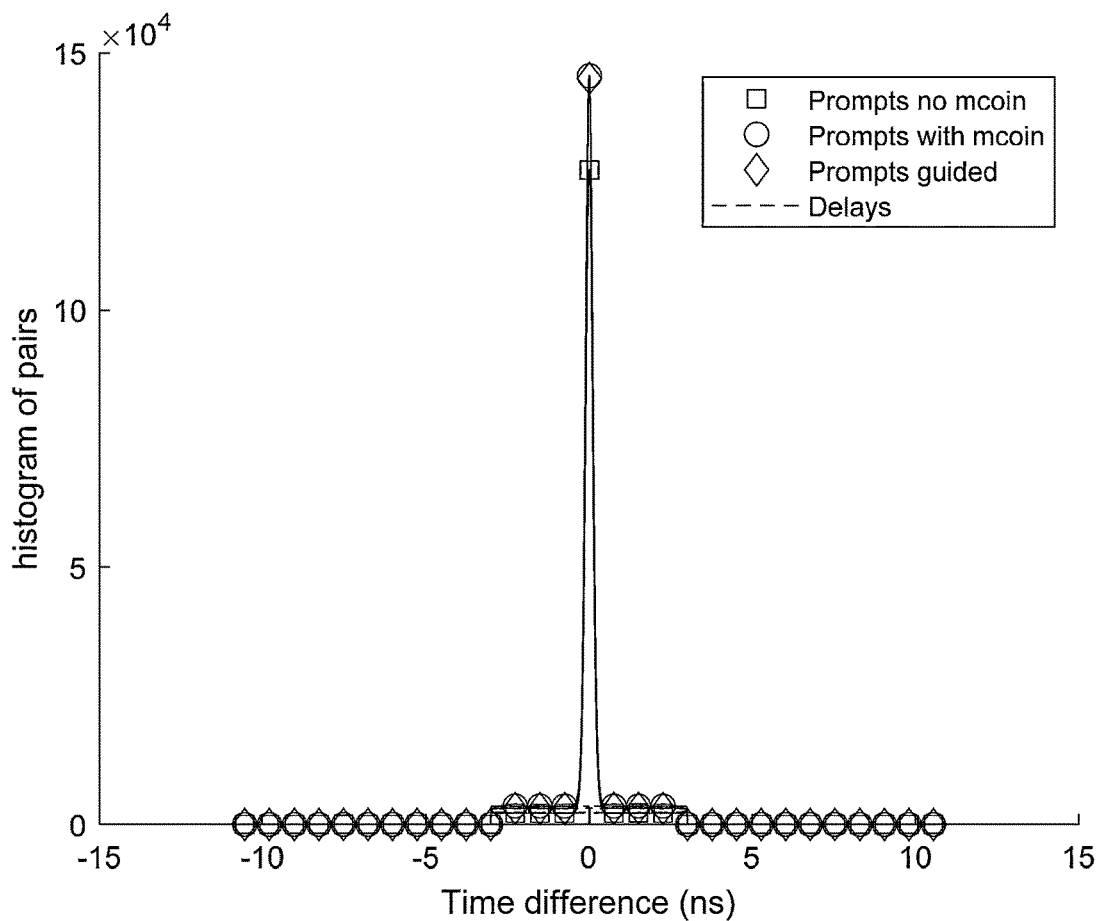
FIG. 5A shows an exemplary graph of the time difference distribution for a real centered line source.

FIG. 5A shows an exemplary graph of the time difference distribution for a real centered line source. FIG. 5B shows a zoom of the peak for the exemplary graph of the time difference distribution of FIG. 5A. FIG. 5C shows a zoom of the baseline for the exemplary graph of the time difference distribution of FIG. 5A. In the above method, guided paring results in the same amount of "prompts" (i.e. true pairs) compared with keeping all the coincidences, thus indicating that the guided pairing can find the trues in the coincidences. Additionally, the amount of prompts via rejecting all coincidences is much lower than both keeping all coincidences or the described guided pairing method. On the other hand, the guided pairing method has less randoms compared with keeping all coincidences.

Figure 5B:
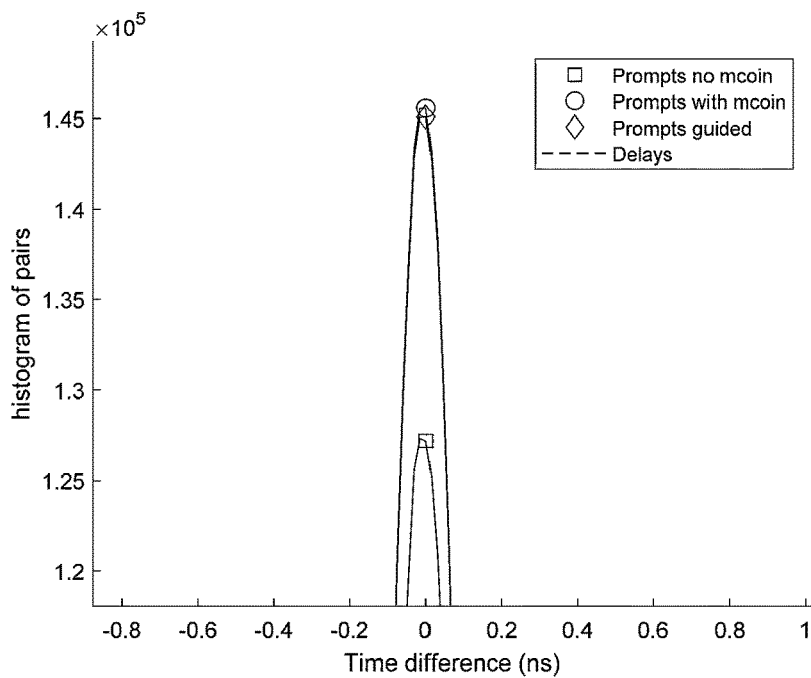
FIG. 5B shows a zoom of the peak for the graph of the time difference distribution of FIG. 5A.
Figure 5C:
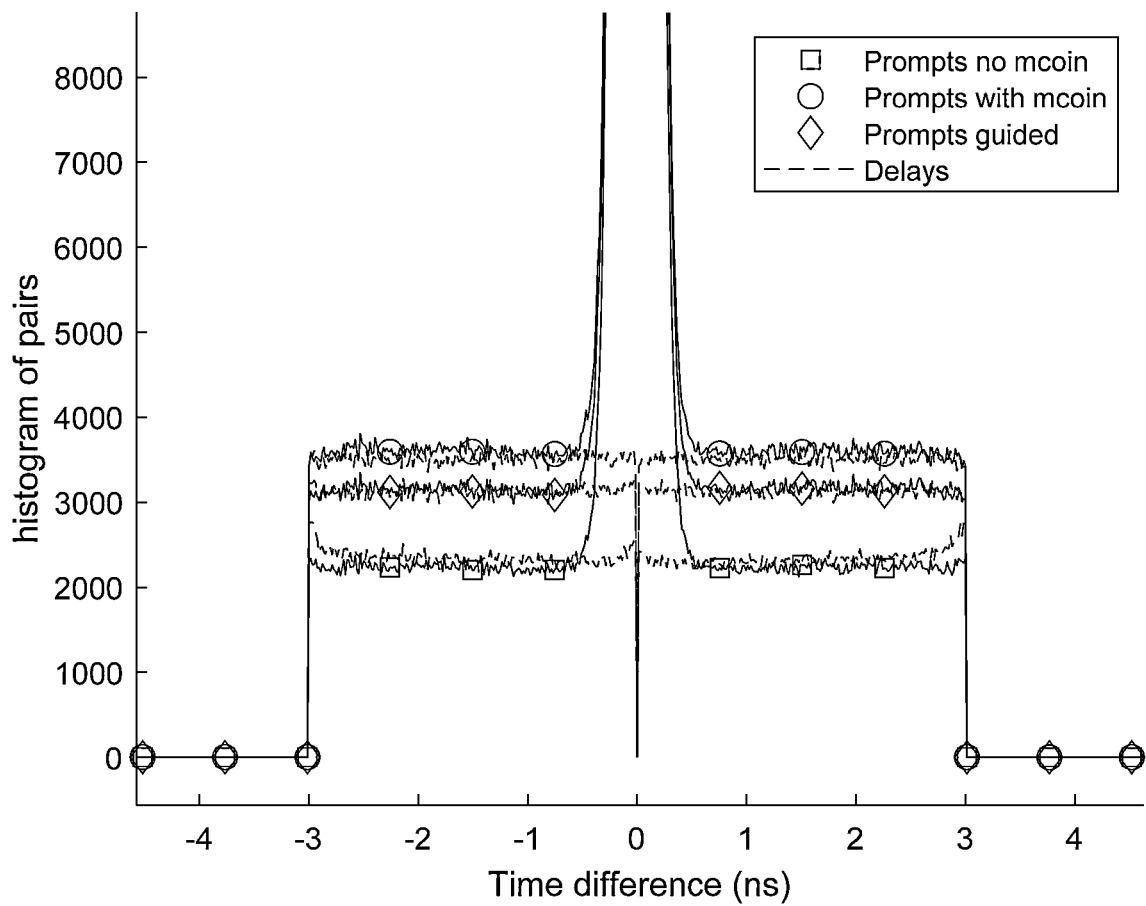
FIG. 5C shows a zoom of the baseline for the graph of the time difference distribution of FIG. 5A.

Notably, the guided pairing results in a similar peak height as keeping all the coincidences in FIG. 5B, while also resulting in a lower baseline as compared to keeping all the coincidences in FIG. 5C. Therefore, this greater difference between peak and baseline demonstrates a higher signal-to-noise ratio by using the guided pairing method as compared to systems using the accept all or reject all coincidences methods. Additionally, the improvement in data quality as described above does not require a significant increase in computation power. However, it should be highlighted that a computational offset can occur wherein rejecting some of the coincidences results in fewer pairs for reconstruction, thus leading to faster reconstruction time. Therefore, as demonstrated, the disclosed method and system herein provides advantages over current imaging systems, including improved accuracy of identifying the true coincidences, improved SNR and data quality, and faster processing and reconstruction time.

Figure 6:
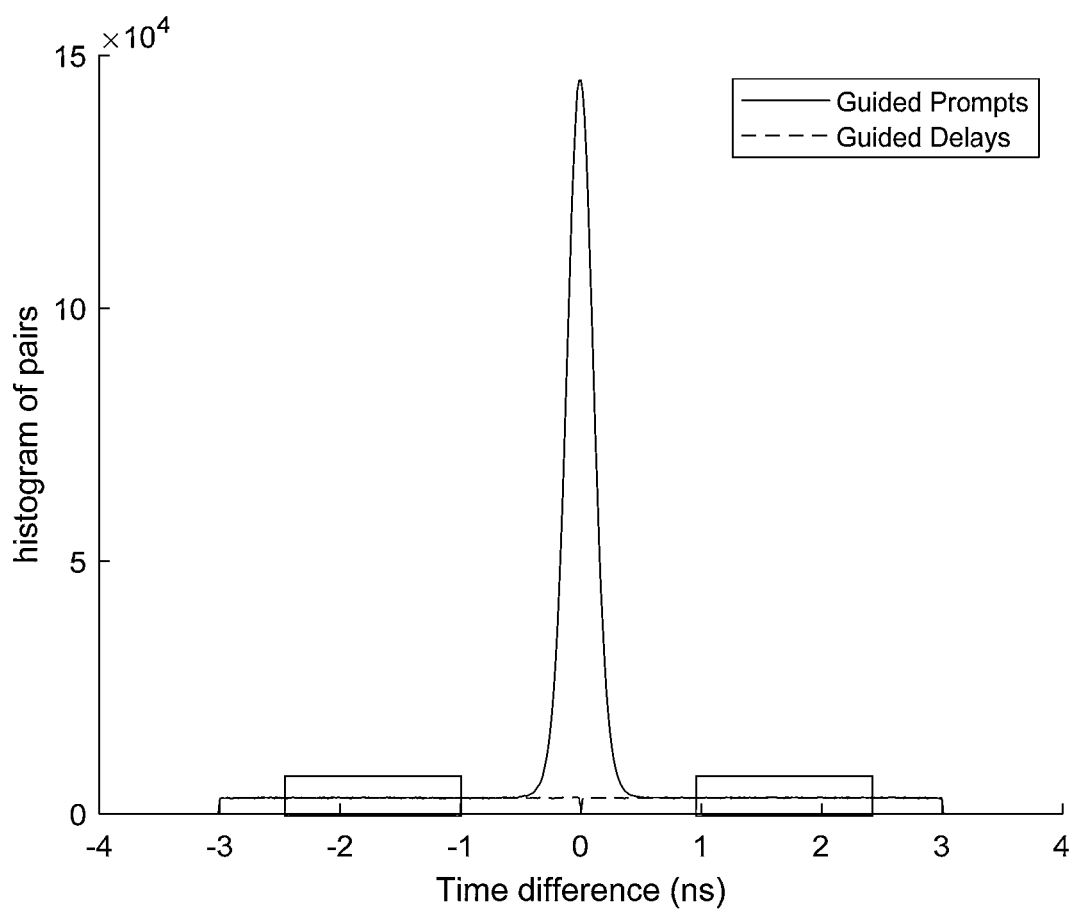
FIG. 6 shows a graph of mean and standard deviation for the exemplary prompt events and the exemplary delay events of FIG. 5A.

FIG. 6 shows a graph of mean and standard deviation for exemplary prompt events and exemplary delay events. To test if there is a bias introduced in the guided pairs data, the mean and standard deviation were calculated for the prompt and delay events within the two windows as shown in FIG. 6 with dashed boxes. The two windows include 200 data points, and result in a mean±standard deviation of: $N_{pp}$=3167±59 (prompt) and $N_{de}$=3124±57 (delay). From this, it can be shown:

$$\Delta N = N_{pp} - N_{de} = 43, \text{ and}$$

$$\sigma(\Delta N) = \sqrt{59^2 + 57^2} = 82$$

where $N_{pp}$ is the mean number of prompt points, $N_{de}$ is the mean number of delay points, $\Delta N$ is a difference between the mean number of prompt points and the mean number of delay points, and $\sigma(\Delta N)$ is the standard deviation of $\Delta N$. Notably, since $\Delta N < \sigma(\Delta N)$, the two tail regions in the black boxes do not have a significant difference, and therefore, no bias is introduced.

FIGS. 7A and 7B show a non-limiting example of a PET scanner 700 that can implement the method 300. The PET scanner 700 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 700.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 7B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 7A and 7B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 7B shows an example of the arrangement of the PET scanner 700, in which the object OBJ to be imaged rests on a table 716 and the GRD modules GRD1 through GRDN are arranged circumferentially around the object OBJ and the table 716. The GRDs can be fixedly connected to a circular component 720 that is fixedly connected to the gantry 740. The gantry 740 houses many parts of the PET imager. The gantry 740 of the PET imager also includes an open aperture through which the object OBJ and the table 716 can pass, and gamma-rays emitted in opposite directions from the object OBJ due to an annihilation event can be detected by the GRDs and timing and energy information can be used to determine coincidences for gamma-ray pairs.

In FIG. 7B, circuitry and hardware is also shown for acquiring, storing, processing, and distributing gamma-ray detection data. The circuitry and hardware include: a processor 770, a network controller 774, a memory 778, and a data acquisition system (DAS) 776. The PET imager also includes a data channel that routes detection measurement results from the GRDs to the DAS 776, the processor 770, the memory 778, and the network controller 774. The DAS 776 can control the acquisition, digitization, and routing of the detection data from the detectors. In one implementation, the DAS 776 controls the movement of the bed 716. The processor 770 performs functions including reconstructing images from the detection data, pre-reconstruction processing of the detection data, and post-reconstruction processing of the image data, as discussed herein.

The processor 770 can be configured to perform various steps of methods 100 and/or 200 described herein and variations thereof. The processor 770 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 770 can execute a computer program including a set of computer-readable instructions that perform various steps of method 100 and/or method 200, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 778 can be a hard disk drive, CD-ROM drive, DVD drive, FLASH drive, RAM, ROM or any other electronic storage known in the art.

The network controller 774, such as an Intel Ethernet PRO network interface card from Intel Corporation of America, can interface between the various parts of the PET imager. Additionally, the network controller 774 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G, 4G, and 5G wireless cellular systems. The wireless network can also be WiFi, Bluetooth, or any other wireless form of communication that is known.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be as set forth in the following parentheticals.

(1) A guided pairing method, comprising: detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determining all coincidences possible based on the more than two singles; generating a weight for said each coincidence of the coincidences based on the determined LORs for said each of the two singles of the plurality of singles; and pairing the more than two singles based on the generated weight for said each coincidence of the coincidences.

(2) The method of (1), wherein the step of generating the weight for said each coincidence of the coincidences further comprises reconstructing a PET image based on the LORs for said each of the two singles of the plurality of singles.

(3) The method of (2), wherein the step of generating the weight for said each coincidence of the coincidences further comprises, for said each coincidence of the coincidences, summing all intensities of all voxels through which the corresponding LOR passes.

(4) The method of (2), further comprising generating a time-of-flight (TOF) kernel for said each coincidence of the coincidences, wherein the step of generating the weight for said each coincidence of the coincidences further comprises summing all intensities of all voxels in the TOF kernel for said each corresponding coincidence of the coincidences.

(5) The method of any one of (1) to (4), wherein pairing the more than two singles further comprises rejecting said all coincidences except for the coincidence having the highest weight.

(6) The method of any one of (1) to (4), wherein pairing the more than two singles further comprises rejecting each coincidence of the coincidences having a corresponding generated weight below a predetermined generated number.

(7) The method of any one of (1) to (6), further comprising applying the weight for said each coincidence of the coincidences as a correction factor during an iteration of the step of reconstructing the PET image based on said each determined coincidence.

(8) An imaging apparatus, comprising: processing circuitry configured to generate a singles list by detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determine all coincidences possible based on the more than two singles; generate a weight for said each coincidence of the coincidences based on the determined LORs for said each of the two singles of the plurality of singles; and pair the more than two singles based on the generated weight for said each coincidence of the coincidence.

(9) The apparatus of (8), wherein the processing circuitry is further configured to generate the weight for said each coincidence of the coincidences by reconstructing a PET image based on the LORs for said each of the two singles of the plurality of singles.

(10) The apparatus of (9), wherein the processing circuitry is further configured to generate the weight for said each coincidence of the coincidences by summing, for said each coincidence of the coincidences, all intensities of all voxels through which the corresponding LOR passes.

(11) The apparatus of (9), wherein the processing circuitry is further configured generate a time-of-flight (TOF) kernel for said each coincidence of the coincidences; and generate the weight for said each coincidence of the coincidences by summing all intensities of all voxels in the TOF kernel for said each corresponding coincidence of the coincidences.

(12) The apparatus of any one of (8) to (11), wherein the processing circuitry is further configured to pair the more than two singles by rejecting said all coincidences except for the coincidence having the highest weight.

(13) The apparatus of any one of (8) to (11), wherein the processing circuitry is further configured to pair the more than two singles by rejecting each coincidence of the coincidences having a corresponding generated weight below a predetermined generated number.

(14) The apparatus of any one of (8) to (13), wherein the processing circuitry is further configured to apply the weight for said each coincidence of the coincidences as a correction factor during an iteration of the step of reconstructing the PET image based on said each determined coincidence.

(15) A non-transitory computer-readable storage medium including executable instructions, which when executed by circuitry, cause the circuitry to perform a method of guided pairing, comprising generating a singles list by detecting a plurality of singles at a plurality of detector elements in a detector array, the plurality of singles falling within a plurality of detection windows; for each detection window of the plurality of detection windows in the singles list having exactly two singles of the plurality of singles, determining the line of responses (LORs) for each of the two singles of the plurality of singles; for each detection window of the plurality of detection windows in the singles list having more than two singles of the plurality of singles, determining all coincidences possible based on the more than two singles; generating a weight for said each coincidence of the coincidences based on the determined LORs for said each of the two singles of the plurality of singles; and pairing the more than two singles based on the generated weight for said each coincidence of the coincidences.

(16) The computer-readable storage medium of (15), wherein the step of generating the weight for said each coincidence of the coincidences further comprises reconstructing a PET image based on the LORs for said each of the two singles of the plurality of singles.

(17) The computer-readable storage medium of (16), wherein the step of generating the weight for said each coincidence of the coincidences further comprises, for said each coincidence of the coincidences, summing all intensities of all voxels through which the corresponding LOR passes.

(18) The computer-readable storage medium of (16), wherein the method further comprises generating a time-of-flight (TOF) kernel for said each coincidence of the coincidences, and the step of generating the weight for said each coincidence of the coincidences further comprises summing all intensities of all voxels in the TOF kernel for said each corresponding coincidence of the coincidences.

(19) The computer-readable storage medium of any one of (15) to (18), wherein pairing the more than two singles further comprises rejecting said all coincidences except for the coincidence having the highest weight.

(20) The computer-readable storage medium of any one of (15) to (18), wherein pairing the more than two singles further comprises rejecting each coincidence of the coincidences having a corresponding generated weight below a predetermined generated number.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed is:

1. A guided pairing method, comprising:
generating a singles list by detecting a plurality of singles at a plurality of detector elements in a detector array, the plurality of singles falling within a plurality of detection windows;
for each detection window of the plurality of detection windows in the singles list having exactly two singles of the plurality of singles, determining a line of response (LOR) for the two singles;
for each detection window of the plurality of detection windows in the singles list having more than two singles of the plurality of singles,
determining all coincidences possible based on the more than two singles;
generating a weight for each coincidence of the coincidences based on the determined LORs; and
pairing the more than two singles based on the generated weight for each coincidence of the coincidences.

2. The method of claim 1, wherein the step of generating the weight for each coincidence of the coincidences further comprises reconstructing a PET image based on the determined LORs.

3. The method of claim 2, wherein the step of generating the weight for each coincidence of the coincidences further comprises, for each coincidence of the coincidences, summing all intensities of all voxels through which the corresponding LOR passes among a plurality of voxels constituting the PET image.

4. The method of claim 3, further comprising generating a time-of-flight (TOF) kernel for each coincidence of the coincidences, wherein
the step of generating the weight for each coincidence of the coincidences further comprises summing all intensities of all voxels in the TOF kernel among a plurality of voxels constituting the PET image for each corresponding coincidence of the coincidences.

5. The method of claim 2, further comprising applying the weight for each coincidence of the coincidences as a correction factor during an iteration of the step of reconstructing the PET image based on each determined coincidence.

6. The method of claim 1, wherein pairing the more than two singles further comprises rejecting all of the coincidences except for a particular coincidence having a highest weight.

7. The method of claim 1, wherein pairing the more than two singles further comprises rejecting each coincidence of the coincidences having a corresponding generated weight below a predetermined generated number.

8. An imaging apparatus, comprising:
processing circuitry configured to
generate a singles list by detecting a plurality of singles at a plurality of detector elements in a detector array, the plurality of singles falling within a plurality of detection windows;
for each detection window of the plurality of detection windows in the singles list having exactly two singles of the plurality of singles, determine a line of response (LOR) for the two singles;
for each detection window of the plurality of detection windows in the singles list having more than two singles of the plurality of singles,
determine all coincidences possible based on the more than two singles;
generate a weight for each coincidence of the coincidences based on the determined LORs; and
pair the more than two singles based on the generated weight for each coincidence of the coincidences.

9. The apparatus of claim 8, wherein the processing circuitry is further configured to generate the weight for each coincidence of the coincidences by reconstructing a PET image based on the determined LORs.

10. The apparatus of claim 9, wherein the processing circuitry is further configured to generate the weight for each coincidence of the coincidences by summing, for each coincidence of the coincidences, all intensities of all voxels through which the corresponding LOR passes among a plurality of voxels constituting the PET image.

11. The apparatus of claim 9, wherein the processing circuitry is further configured to
generate a time-of-flight (TOF) kernel for each coincidence of the coincidences; and
generate the weight for each coincidence of the coincidences by summing all intensities of all voxels in the TOF kernel among a plurality of voxels constituting the PET image for each corresponding coincidence of the coincidences.

12. The apparatus of claim 9, wherein the processing circuitry is further configured to apply the weight for each coincidence of the coincidences as a correction factor during an iteration of the step of reconstructing the PET image based on each determined coincidence.

13. The apparatus of claim 8, wherein the processing circuitry is further configured to pair the more than two singles by rejecting all of the coincidences except for a particular coincidence having a highest weight.

14. The apparatus of claim 8, wherein the processing circuitry is further configured to pair the more than two singles by rejecting each coincidence of the coincidences having a corresponding generated weight below a predetermined generated number.

15. A non-transitory computer-readable storage medium including executable instructions, which when executed by circuitry, cause the circuitry to perform a method of guided pairing, comprising:
generating a singles list by detecting a plurality of singles at a plurality of detector elements in a detector array, the plurality of singles falling within a plurality of detection windows;
for each detection window of the plurality of detection windows in the singles list having exactly two singles of the plurality of singles, determining a line of response (LOR) for the two singles;
for each detection window of the plurality of detection windows in the singles list having more than two singles of the plurality of singles,
determining all coincidences possible based on the more than two singles;
generating a weight for said coincidence of the coincidences based on the determined LORs; and
pairing the more than two singles based on the generated weight for each coincidence of the coincidences.

16. The computer-readable storage medium according to claim 15, wherein the step of generating the weight for each coincidence of the coincidences further comprises reconstructing a PET image based on the determined LORs.

17. The computer-readable storage medium according to claim 16, wherein the step of generating the weight for each coincidence of the coincidences further comprises, for each coincidence of the coincidences, summing all intensities of all voxels through which the corresponding LOR passes among a plurality of voxels constituting the PET image.

18. The computer-readable storage medium according to claim 16, wherein the method further comprises generating a time-of-flight (TOF) kernel for each coincidence of the coincidences, and the step of generating the weight for each coincidence of the coincidences further comprises summing all intensities of all voxels in the TOF kernel among a plurality of voxels constituting the PET image for each corresponding coincidence of the coincidences.

19. The computer-readable storage medium according to claim 15, wherein pairing the more than two singles further comprises rejecting all of the coincidences except for a particular coincidence having a highest weight.

20. The computer-readable storage medium according to claim 15, wherein pairing the more than two singles further comprises rejecting each coincidence of the coincidences having a corresponding generated weight below a predetermined generated number.

\* \* \* \* \*